US012721508B1

(12) United States Patent
Mau et al.

(10) Patent No.: US 12,721,508 B1
(45) Date of Patent: Sep. 1, 2026

(54) TISSUE CAPTURE DEVICE HAVING FASTENERS WITH SHAPE-CHANGING PROPERTIES

(71) Applicant: NUtech Ventures, Lincoln, NE (US)

(72) Inventors: Musharrat Mustaree Mau, Lincoln, NE (US); Benjamin S. Terry, Lincoln, NE (US)

(73) Assignee: NUtech Ventures, Lincoln, NE (US)

( * ) Notice: Subject to any disclaimer, the term of this patent is extended or adjusted under 35 U.S.C. 154(b) by 283 days.

(21) Appl. No.: 18/227,649

(22) Filed: Jul. 28, 2023

Related U.S. Application Data

(60) Provisional application No. 63/370,514, filed on Aug. 5, 2022.

(51) Int. Cl.

| | |
|---|---|
| ***A61B 1/00*** | (2006.01) |
| ***A61B 1/04*** | (2006.01) |
| ***A61B 10/02*** | (2006.01) |
| ***A61B 10/04*** | (2006.01) |

(52) U.S. Cl.
CPC ............ *A61B 1/041* (2013.01); *A61B 1/0011* (2013.01); *A61B 1/00121* (2013.01); *A61B 10/02* (2013.01); *A61B 10/0233* (2013.01); *A61B 10/04* (2013.01)

(58) Field of Classification Search
CPC ... A61B 1/041; A61B 1/0011; A61B 1/00121; A61B 10/04; A61B 10/0233; A61B 10/02
See application file for complete search history.

(56) References Cited

U.S. PATENT DOCUMENTS

| | | | | |
|---|---|---|---|---|
| 2011/0092990 A1* | 4/2011 | Gambale | A61B 17/1114 | 606/144 |
| 2012/0184957 A1* | 7/2012 | Saleh | A61B 17/221 | 606/49 |
| 2012/0265217 A1* | 10/2012 | Drews | A61B 10/0266 | 606/133 |
| 2016/0000312 A1* | 1/2016 | Seibel | A61B 1/043 | 600/109 |
| 2023/0263509 A1* | 8/2023 | Yangdai | A61B 1/045 | 600/582 |
| 2023/0404428 A1* | 12/2023 | Stine | A61B 1/00016 | |
| 2025/0098948 A1* | 3/2025 | Duan | A61B 1/00034 | |

* cited by examiner

*Primary Examiner* — Michael J Carey
(74) *Attorney, Agent, or Firm* — Suiter Swantz IP

(57) ABSTRACT

A tissue capture device is disclosed. The tissue capture device may include a frame, wherein the frame defines an orifice. The tissue capture device may include a set of fasteners disposed within the orifice, wherein at least some of the fasteners of the set of fasteners are formed from a material displaying one or more shape-changing properties, wherein the one or more shape-changing properties comprises a transition from a deformed phase to a non-deformed phase.

19 Claims, 6 Drawing Sheets

TISSUE CAPTURE DEVICE HAVING FASTENERS WITH SHAPE-CHANGING PROPERTIES

CROSS-REFERENCE TO RELATED APPLICATIONS

The present application claims the benefit under 35 U.S.C. § 119 (e) of U.S. Provisional Application No. 63/370,514, filed Aug. 5, 2022, which is incorporated herein by reference in the entirety.

TECHNICAL FIELD

The present disclosure relates generally to medical examinations performed with capsule-based endoscopy and, more particularly, to capsule endoscopy performed with a tissue capture device equipped with fasteners having shape-changing properties.

BACKGROUND

A capsule endoscope (CE) (e.g., a device used in capsule endoscopy) is one of the most common non-invasive clinical tools in the evaluation of gastrointestinal (GI) tract disease or other medical concerns, such as, but not limited to, GI bleeding, inflammatory bowel disease and Crohn's disease, cancer, celiac disease, and/or polyps. Most CE sensors are passive devices that move through the GI tract by peristalsis and are typically cycled out of a subject's body within a day and may only be present in an area of interest (e.g., a particular portion of the GI tract) for several hours at most. However, it may be desirable for the CE to be present in an area of interest for longer than several hours. Therefore, there is a need to provide a device and method that cures the deficiencies of current CEs as identified above.

SUMMARY

A tissue capture device is disclosed, in accordance with embodiments of the present disclosure. In embodiments, the tissue capture device includes a frame, wherein the frame defines an orifice. In embodiments, the tissue capture device includes a set of fasteners disposed within the orifice, wherein at least some of the fasteners of the set of fasteners are formed from a material displaying one or more shape-changing properties, wherein the one or more shape-changing properties comprises a transition from a deformed phase to a non-deformed phase.

A capsule endoscopy system is disclosed, in accordance with embodiments of the present disclosure. In embodiments, the capsule endoscopy system includes a tissue capture device. In embodiments, the tissue capture device includes a frame, wherein the frame defines an orifice. In embodiments, the tissue capture device includes a set of fasteners disposed within the orifice, wherein at least some of the fasteners of the set of fasteners are formed from a material displaying one or more shape-changing properties, wherein the one or more shape-changing properties comprises a transition from a deformed phase to a non-deformed phase. In embodiments, the capsule endoscopy system includes a capsule endoscope.

A method is disclosed, in accordance with embodiments of the present disclosure. in embodiments, the method includes introducing a capsule endoscope to a gastrointestinal (GI) tract, wherein a tissue capture device is coupled to the capsule endoscope. In embodiments, the method includes reaching an area of interest within the GI tract. In embodiments, the method includes inserting a set of fasteners of the tissue capture device into tissue of the GI tract in the area of interest, wherein the fasteners are inserted into the tissue in a deformed state. In embodiments, the method includes securing the tissue capture device to the tissue of the GI tract by transitioning the set of fasteners of the tissue capture device from the deformed state to the non-deformed state.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF DRAWINGS

The numerous advantages of the disclosure may be better understood by those skilled in the art by reference to the accompanying figures.

DETAILED DESCRIPTION

Reference will now be made in detail to the subject matter disclosed, which is illustrated in the accompanying drawings. The present disclosure has been particularly shown and described with respect to certain embodiments and specific features thereof. The embodiments set forth herein are taken to be illustrative rather than limiting. It should be readily apparent to those of ordinary skill in the art that various changes and modifications in form and detail may be made without departing from the spirit and scope of the disclosure.

The present disclosure discloses a tissue capture device that can assist with gastrointestinal (GI) tract monitoring. As discussed herein, a tissue capture device can include a set of fasteners that have shape-changing properties. In embodiments, the set of fasteners is a set of micro-needles. For example, prior to tissue capture, the fasteners can be oriented at an angle relative to the tissue and, after tissue capture, the fasteners can be oriented at least substantially parallel to the tissue. Tips of the fasteners can also be aligned such that a radius of the circle inscribed by the tips approaches zero.

For the purposes of the present disclosure, the phrase tissue capture broadly relates to attaching a device to tissue (e.g., attachment to GI tissue via fasteners).

Referring now to FIGS. 1A-5, a tissue capture device 100 is disclosed, in accordance with embodiments of the present disclosure.

Figure 1A:
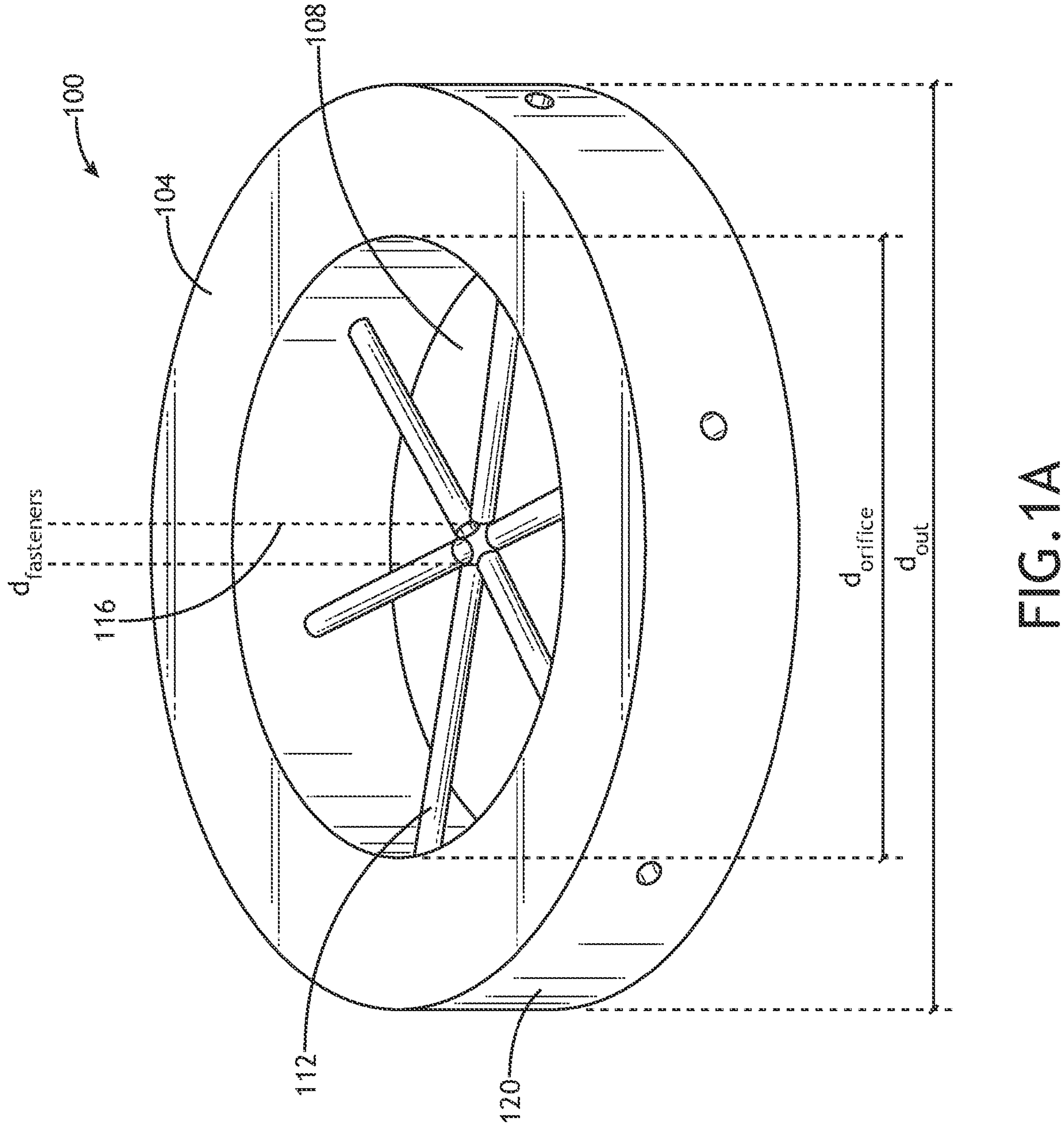
FIG. 1A is a perspective view of a tissue capture device with fasteners in a non-deformed phase, in accordance with one or more embodiments of the present disclosure.

FIG. 1A is a perspective view of a tissue capture device 100 with fasteners 112 in a non-deformed phase, in accordance with one or more embodiments of the present disclosure.

FIG. 1A illustrates a tissue capture device 100, in accordance with one or more embodiments of the present disclosure. The tissue capture device 100 may be configured to disengage from an orally-administrable capsule (e.g., a capsule endoscope (CE)). This tissue capture device 100 may disengage from the CE after, or substantially at the same time, the tissue capture device 100 attaches to GI tissue at a selected attachment site, or region, within a GI tract of an individual. For example, the selected attachment site may be a site at or near a location where further medical analysis is needed within the GI tract.

In embodiments, the tissue capture device 100 includes a frame 104. The frame 104 of the tissue capture device 100 may define an orifice 108 (e.g., a hole), where the perimeter of the hole is formed by the frame 104. For example, the frame 104 and the orifice 108 may both be circular. Further, the orifice 108 may the same or a different shape than the frame 104. The frame 104 may be made of any material suitable for medical applications. For example, the frame 104 may be made from polymethyl methacrylate.

In embodiments, the tissue capture device 100 includes a set of fasteners 112. Broadly speaking, the set of fasteners 112 may be any set of members that may secure a device (e.g., the frame 104) to soft tissue. As a nonlimiting example, one or more of the fasteners 112 may be formed as a micro-needle. For instance, each of the fasters 112 may be formed as a micro-needle.

The set of fasteners 112 may be disposed within the orifice 108. Within the orifice 108, the set of fasteners 112 may be equally spaced. The set of fasteners 112 may be configured to connect the tissue capture device 100 to GI tissue.

In embodiments, the fasteners 112 may have one or more shape-changing properties. In this way, the fasteners 112 may be made from a memory metal (e.g., a shape-memory alloy). The memory metal may be any material that displays shape-changing properties (e.g., a transition between a first state and a second state). For instance, the shape of the fasteners 112 may change based on environmental conditions of the fasteners 112. In embodiments, the fasteners 112 may be configured such that the fasteners 112 change shape during tissue capture (e.g., the fasteners 112 change shape to attach the tissue capture device 100 to tissue). In an example implementation, the fasteners 112 comprise micro-needles formed from nitinol (e.g., an alloyed memory metal made from nickel and titanium). Typically, memory metals (e.g., including nitinol) will exhibit two phases, an austenite phase, and a martensite phase. Further, memory metals (e.g., including nitinol) may display shape memory, wherein the memory metal will return to a predefined shape when certain conditions are met. In embodiments, the memory metal micro-needles may transition between the austenite phase and the martensite phase due to stress. For example, the memory metal micro-needles may transition from a non-deformed orientation (e.g., the austenite phase) to a deformed orientation (e.g., the martensite phase) under stress induced by one or more factors such as, but not limited to, a transition temperature and/or a biasing member. During manufacturing of the tissue capture device 100, the memory metal micro-needles may be initially fabricated in the austenite phase and maintain attachment to the frame 104 while in the austenite phase. While the specifics of this disclosure have been described with reference to memory metal micro-needles, such a configuration should be interpreted as illustrative only and not limiting the scope of the present disclosure, as any material displaying the ability to transition from a deformed state to a non-deformed state is within the scope of the disclosure.

The memory metal may include alloys such as, but not limited to nitinol (e.g., an alloy of nickel and titanium), a copper, zinc, and aluminum (Cu—Zn—Al) alloy, a copper, aluminum, and nickel (Cu—Al—Ni) alloy, an iron, manganese and silicon (Fe—Mn—Si) alloy, or the like.

As shown, the fasteners 112 may be attached to a sidewall 116 of the frame 104. For example, the fasteners 112 may extend from the sidewall 116 into the orifice 108 and form an inscribed circle. In embodiments, the tissue capture device 100 may include, for example, at least three (3), at least four (4), at least five (5), or at least six (6) fasteners 112 to enable sufficient anchoring to the GI tissue without causing damage to the tissue at the attachment site. It has been found that, in some embodiments, six (6) fasteners 112 provide sufficient anchoring without any significant damage to the attached tissue.

The orifice 108 of the tissue capture device 100 may have an orifice diameter ($d_{orifice}$) of at least approximately six millimeters (6 mm). The frame 104 of the tissue capture device 100 may have an outer diameter 120 ($d_{out}$) (e.g., a diameter defined by the frame 104) that may be at least approximately nine millimeters (9 mm). The fasteners 112 may have a length of at least approximately two and three quarters millimeters (2.75 mm) and a diameter (e.g., a width) of approximately one quarter millimeter (0.25 mm). However, the previously discussed dimension should be interpreted as exemplary only, and not limiting on the scope of the present disclosure.

The properties (e.g., the length, diameter, number of micro-needles, or the like) of the tissue capture device 100 may be selected to increase an attachment duration of the tissue capture device 100 to the GI tissue. For example, empirical analysis has shown that attachment duration increased when the fasteners 112 were oriented generally parallel to the tissue and when a radius of the circle inscribed by the fastener 112 tips approached zero (0). In embodiments, the diameter of the circle inscribed by the fastener 112 tips (e.g., $d_{fasteners}$) may be 0.25 millimeters, though this dimension should be interpreted as exemplary only and not limiting. For example, these properties demonstrated that the tissue capture device 100 may allow for a more relatively complete tissue capture without penetrating relatively deeply into the submucosa or other layers of the GI tissue.

Within the present context, the frame 104 of the tissue capture device 100 may comprise an outer diameter to orifice diameter aspect ratio of 3:2. A fastener 112 may comprise a length to width aspect ratio of 11:1.

Figure 1B:
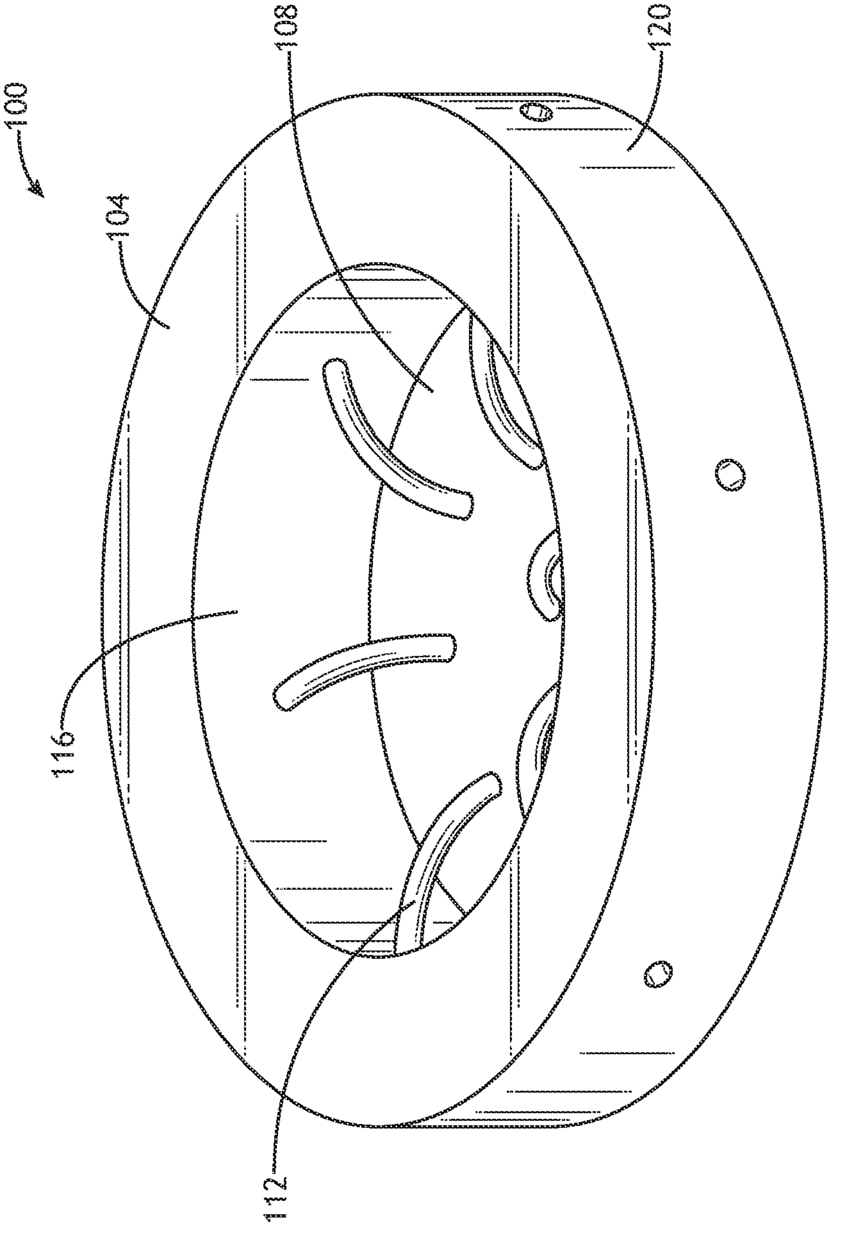
FIG. 1B is a perspective view of a tissue capture device with fasteners in a deformed phase, in accordance with one or more embodiments of the present disclosure.

FIG. 1B is a perspective view of a tissue capture device 100 with fasteners 112 in a deformed phase, in accordance with one or more embodiments of the present disclosure.

For example, in FIG. 1B, the fasteners 112 (e.g., the micro-needles) are deformed such that they are pointed down, in contrast to the flat fasteners 112 depicted in FIG. 1A. In this way, the deformed fasteners 112 may easily enter (e.g., penetrate) tissue in the GI tract. Further, the transition of the fasteners 112 from the deformed phase (e.g., the tissue capture device 100 of FIG. 1B) to the non-deformed phase (e.g., the tissue capture device 100 of FIG. 1A) may serve to lock the tissue capture device 100 onto the GI tissue.

Figure 2:
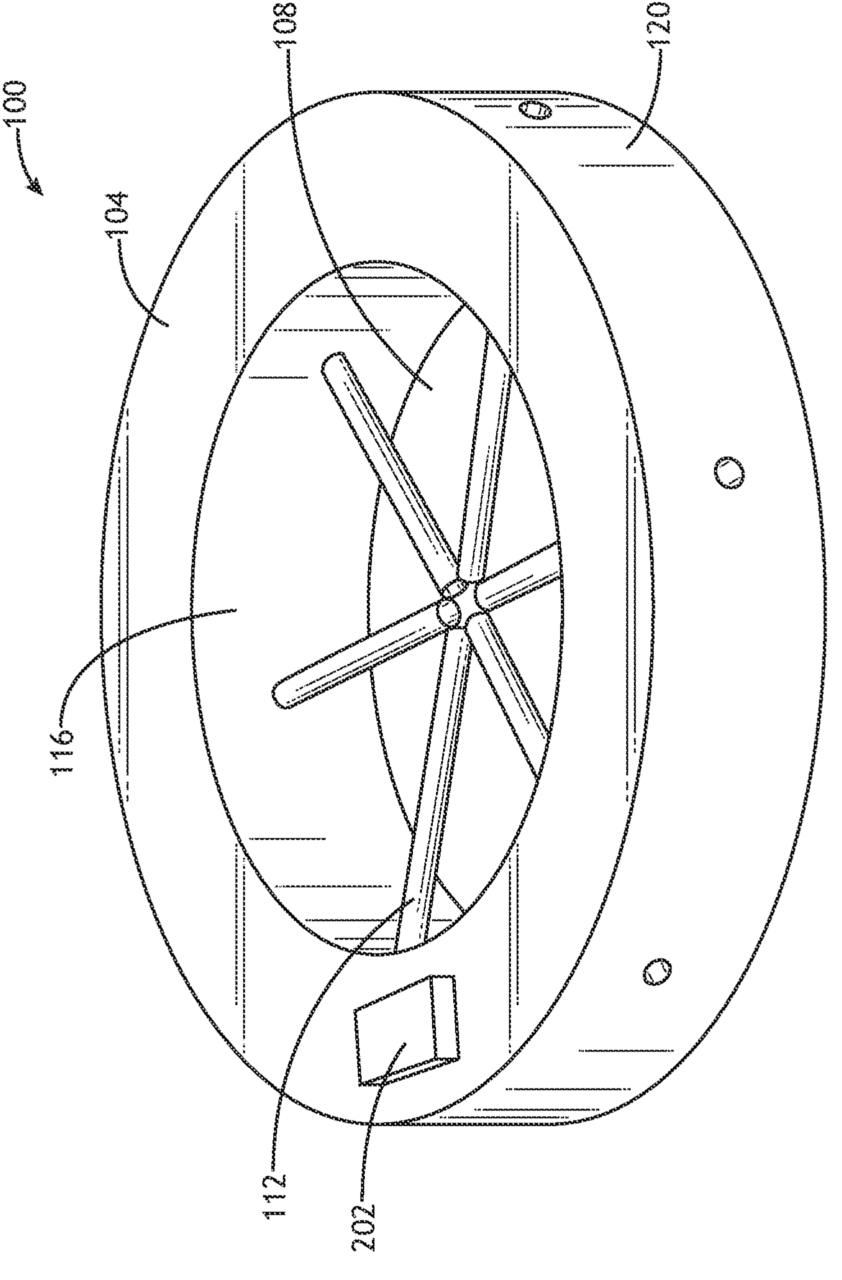
FIG. 2 is a perspective view of a tissue capture device where a medical device is mounted to a surface of the tissue capture device, in accordance with one or more embodiments of the present disclosure.

FIG. 2 is a perspective view of a tissue capture device 100 where a medical device 202 is mounted to a surface of the tissue capture device 100, in accordance with one or more embodiments of the present disclosure.

FIG. 2 illustrates another example implementation of the tissue capture device 100. As shown, the tissue capture device 100 may also include a medical device 202. In embodiments, the medical device 202 may be coupled to or integrated with the tissue capture device 100 for long term (e.g., several days or weeks long) implantation within the GI tract of an individual at the attachment site. For instance, the medical device 202 can be mounted (e.g., coupled) to a surface of the frame 104 using a suitable adhesive. Further, the medical device 202 may be coupled to the surface of the frame 104 via mechanical means, such as embedded or otherwise fastened to the surface. In embodiments, the medical device 202 can include a biometric sensor, including, but not limited to, a thermal sensor, a pH sensor, a pressure sensor, an analyte sensor, or any other deployable, in vivo detector or sensor. In embodiments, the medical device 202 may be a drug delivery device that releases medication. For example, the drug delivery device may release medication at predetermined time intervals.

Figure 3:
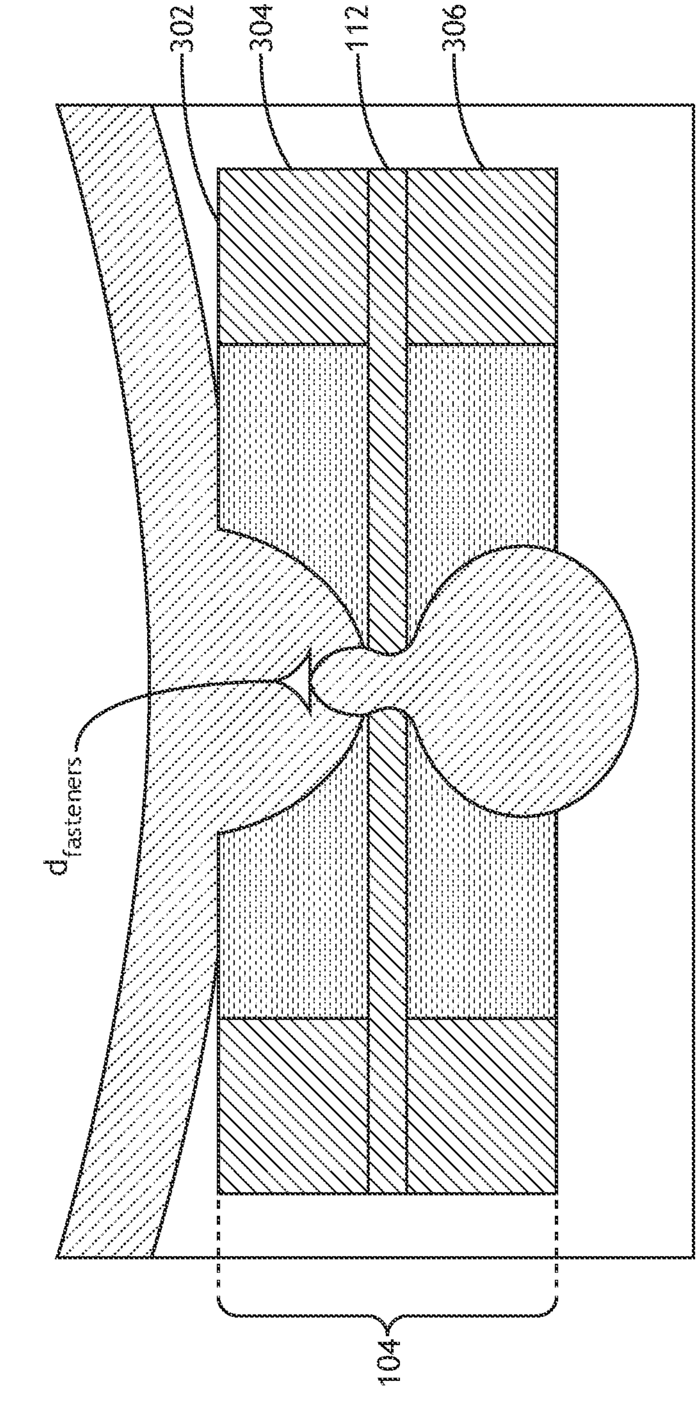
FIG. 3 is a cross-sectional view of a tissue capture device, in accordance with one or more embodiments of the present disclosure.

FIG. 3 is a cross-sectional view of a tissue capture device 100, in accordance with one or more embodiments of the present disclosure.

FIG. 3 illustrates an example cross-sectional view of the tissue capture device 100 attached to a portion of the GI tract. As shown, when attached to the GI tract, the fasteners 112 are in the austenite phase (e.g., at least substantially oriented parallel to the tissue). In other words, the fasteners 112 can be oriented parallel to a plane that is defined as parallel with a first surface 302 of the frame 104. During delivery of the tissue capture device 100, the fasteners are deformed to the martensite phase such that the fasteners are deflected, i.e., non-parallel, with respect to the tissue and/or the first surface 302 of the frame 104. In an example implementation, the delivery device (e.g., and orally-administrable capsule (e.g., a capsule endoscope)) may include one or more biasing members that bias the fasteners 112 into martensite phase (e.g., a deformed phase). As such, upon ejection of the tissue capture device 100 from the delivery device, the fasteners 112 may transition to the austenite phase while capturing the tissue (e.g., attaching the tissue capture device 100 to the tissue) within the GI tract.

For example, when in the martensite phase (e.g., the deformed phase), the fasteners 112 may be able to enter into the GI tissue and the transition to the austenite phase (e.g., the non-deformed phase) may capture the tissue. Further, the austenite phase may hold the tissue capture device 100 in place on the GI tissue.

With continuing reference to FIG. 3, the tissue capture device 100 may be constructed by positioning the fasteners 112 between a first frame portion 304 and a second frame portion 306. For instance, the first frame portion 304 and the second frame portion 306 may be constructed via a suitable additive manufacturing process (e.g., 3-dimensional (3D) printing, vat polymerization, material jetting, binder jetting, material extrusion, powder bed fusion, sheet lamination, directed energy deposition, or the like), or the like. Once formed, the fasteners 112 can be positioned between frame portions 304, 306 and attached to the frame portions 304, 306 using any suitable adhesive material or mechanical means. As shown, the fasteners 112 are positioned such that the diameter ($d_{fasteners}$) of the circle inscribed by the fastener 112 tips approaches zero (0). For instance, the diameter ($d_{fasteners}$) may be 0.25 mm or less.

Figure 4:
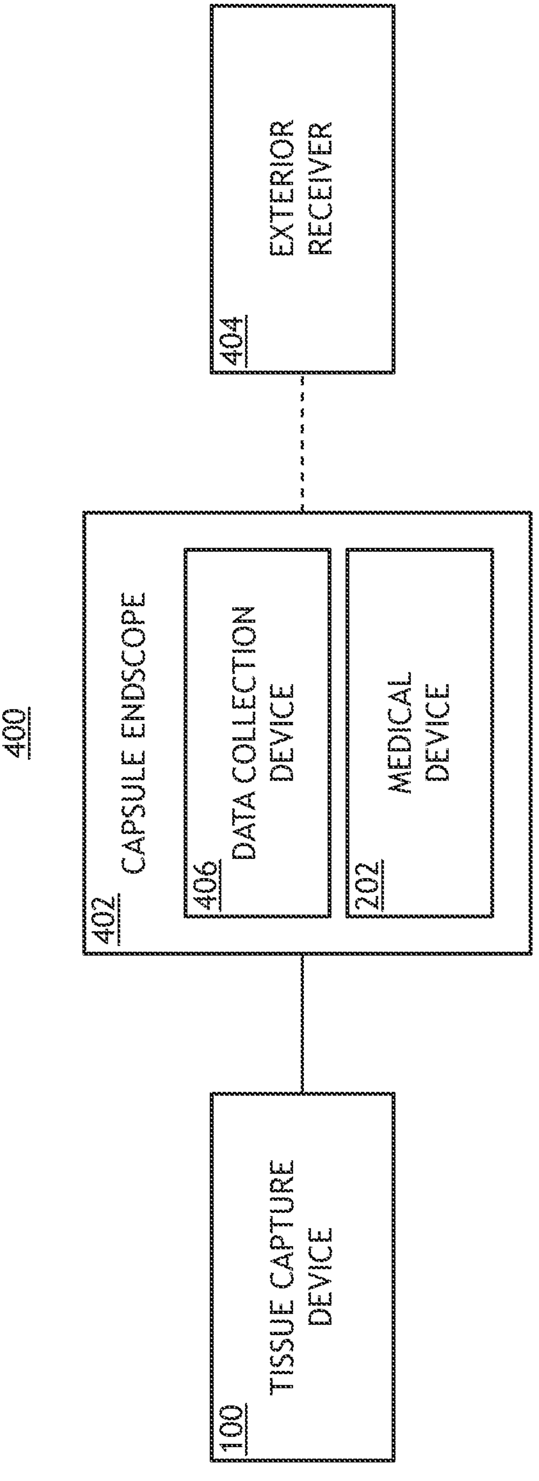
FIG. 4 is a block diagram of a capsule endoscopy system including the tissue capture device, in accordance with one or more embodiments of the present disclosure.

FIG. 4 is a block diagram of a capsule endoscopy system 400 including the tissue capture device 100, in accordance with one or more embodiments of the present disclosure.

In embodiments, the capsule endoscopy system 400 includes a capsule endoscope 402. A capsule endoscope 402 may be a small device. For example, a capsule endoscope 402 may be approximately the size of a pill such that a human can swallow it to permit data collection in a GI tract. This may provide non-invasive means of observing the GI tract or provide the ability to collect data from parts of the GI tract that would otherwise be difficult to observe.

The capsule endoscope 402 may include a data collection device 406 (e.g., a camera, other data collection devices (e.g., one or more sensors)) and/or medical devices 202 (e.g., the same or similar medical devices to those that may be integrated into the tissue capture device 100) to collect data from inside the GI tract or administer a treatment. The capsule endoscope 402 may either store the collected data internally or transmit the data to an exterior receiver 404 located outside the GI tract (e.g., outside the individual). The medical devices 202 that are part of the capsule endoscope may be the same type of medical devices 202 or different medical devices 202 as previously discussed herein with reference to the tissue capture device. For example, with reference to the capsule endoscope 402, the medical device 202 may specifically be configured to administer a treatment within the GI tract, while the data collection device 406 may be configured to collect data from within the GI tract.

Typically, capsule endoscopes 402 are propelled through the GI tract via peristalsis. As a result, a capsule endoscope 402 may only be in the individual for approximately eight hours. Because an area of interest for the capsule endoscope 402 may be only a small portion of the GI tract (e.g., the small intestine, the large intestine, or the like), the time the capsule endoscope 402 spends in the area of interest may be significantly less than the approximately eight hours it spends within the individual. At times, the limited presence of the capsule endoscope 402 within the area of interest may be acceptable, however, there may be a need for the capsule endoscope 402 to remain in the area of interest for longer periods of time.

In embodiments, the capsule endoscopy system 400 may further include the tissue capture device 100 as disclosed herein. The tissue capture device 100 may be coupled to the capsule endoscope 402, or otherwise integrated into the capsule endoscope 402. When the capsule endoscope 402 reaches an area of interest within the GI tract, the tissue capture device 100 may attach to tissue of the GI tract. For example, the tissue capture device 100 may approach and make contact with the tissue when it is in the deformed state (e.g., the fasteners 112 are pointed towards the tissue). After making contact and penetrating the tissue, the fasteners 112 may transition to the non-deformed state such that the tissue capture device 100 becomes attached to the tissue. During the attachment to the tissue, the tissue capture device 100 may either remain coupled to the capsule endoscope 402 (e.g., keep the capsule endoscope 402 for a longer period of time) or decouple from the capsule endoscope (e.g., attach the tissue capture device 100 to the tissue but allow the capsule endoscope to continue through the GI tract). In this way, the capsule endoscope 402 may be permitted to perform further observation or data collection in the area of interest or the tissue capture device may remain to perform operations (e.g., observation or treatment) via a medical device 202.

In embodiments, the capsule endoscopy system 400 includes an exterior receiver 404 communicatively coupled to the capsule endoscope 402. For example, the capsule endoscope 402 may transmit the data collected to the exterior receiver 404 such that it may be analyzed. However, some capsule endoscopes 402 are have data storage capabilities, and thus an exterior receiver may not be necessary to store the data collected by the capsule endoscope 402.

Figure 5:
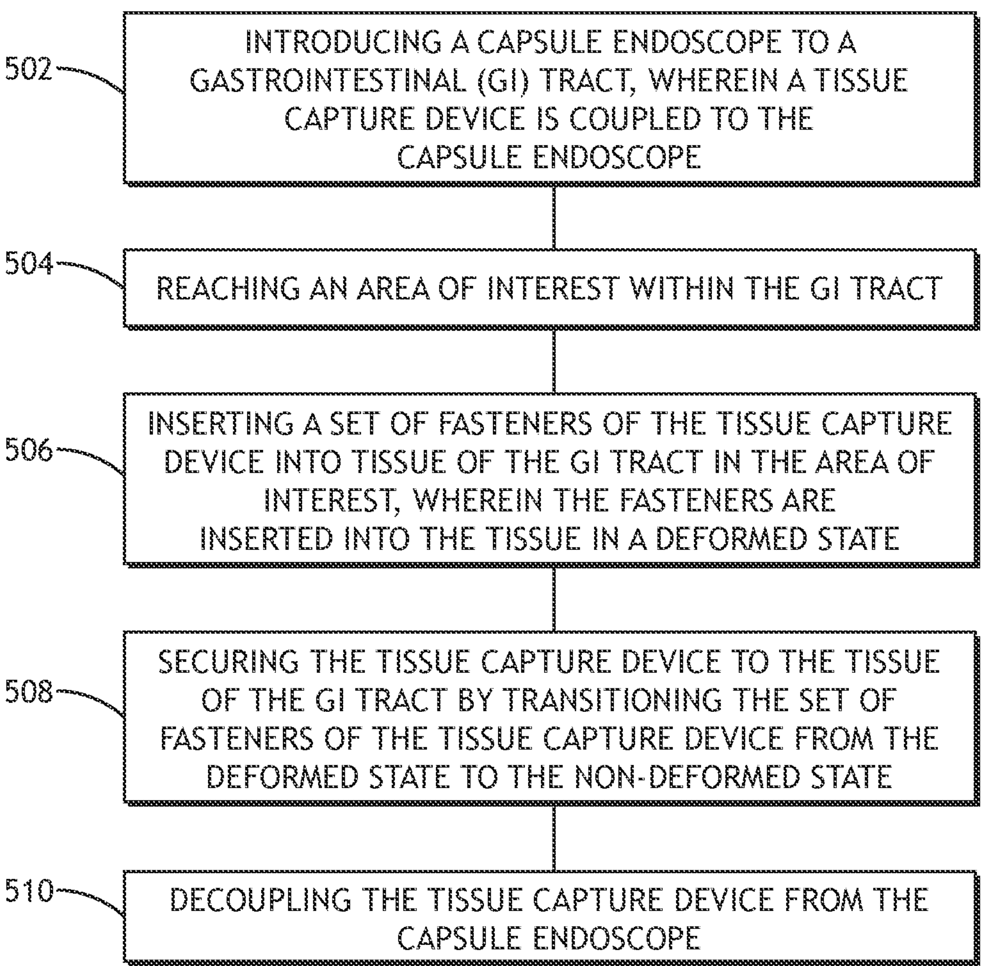
FIG. 5 is a flow diagram of a method for capsule endoscopy, in accordance with one or more embodiments of the present disclosure.

FIG. 5 is a flow diagram of a method 500 for capsule endoscopy, in accordance with one or more embodiments of the present disclosure. Applicant notes that the embodiments and enabling technologies described previously herein in the context of the tissue capture device 100 and the capsule endoscopy system 400 should be interpreted to extend to the method 500. It is further noted, however, that the method 500 is not limited to the architecture of the tissue capture device 100 and the capsule endoscopy system 400.

In embodiments, the method 500 includes a step 502 of introducing a capsule endoscope to a gastrointestinal (GI) tract, wherein a tissue capture device is coupled to the capsule endoscope. For example, the capsule endoscope may be introduced to the GI tract by having a patient swallow the capsule endoscope.

In embodiments, the method 500 includes a step 504 of reaching an area of interest within the GI tract. For example, after swallowing the capsule endoscope, the capsule endoscope may move through the GI tract via peristalsis until the capsule endoscope arrives at the area of interest.

In embodiments, the method 500 includes a step 506 of inserting a set of fasteners of the tissue capture device into tissue of the GI tract in the area of interest, wherein the fasteners are inserted into the tissue in a deformed state. For example, in the deformed state, the fasteners (e.g., the memory metal micro-needles) may be oriented in such a manner that they are largely perpendicular to the tissue of the GI tract. In this way, the fasteners may be easily inserted into (e.g., penetrate) the tissue of the GI tract.

In embodiments, the method 500 includes a step 508 of securing the tissue capture device to the tissue of the GI tract by transitioning the set of fasteners of the tissue capture device from the deformed state to the non-deformed state. For example, after the fasteners have penetrated the tissue, the fasteners may transition from a deformed state (e.g., largely perpendicular to the tissue) to a non-deformed state (e.g., largely parallel to the tissue). In this way, the fasteners may secure the tissue capture device into place on the tissue of the GI tract.

In embodiments, the method 500 includes an optional step 510 of decoupling the tissue capture device from the capsule endoscope. For example, it may be desirable to have the tissue capture device secured to the tissue of the GI tract independent of the capsule endoscope or the capsule endoscopy system (e.g., when the tissue capture device includes a medical device). In this way, the capsule endoscope may continue to pass through the GI tract while the tissue capture device remains in place on the GI tissue. However, there may be instances where it is desirable to keep the tissue capture device coupled to the capsule endoscope throughout the time when the tissue capture device is secured to the tissue of the GI tract.

The herein described subject matter sometimes illustrates different components contained within, or connected with, other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "connected" or "coupled" to each other to achieve the desired functionality, and any two components capable of being so associated can also be viewed as being "couplable" to each other to achieve the desired functionality. Specific examples of couplable include but are not limited to physically interactable and/or physically interacting components and/or wirelessly interactable and/or wirelessly interacting components and/or logically interactable and/or logically interacting components.

It is believed that the present disclosure and many of its attendant advantages will be understood by the foregoing description, and it will be apparent that various changes may be made in the form, construction, and arrangement of the components without departing from the disclosed subject matter or without sacrificing all of its material advantages. The form described is merely explanatory, and it is the intention of the following claims to encompass and include such changes. Furthermore, it is to be understood that the invention is defined by the appended claims.

What is claimed:

1. A tissue capture device comprising:

a frame, wherein the frame defines an orifice; and a set of fasteners disposed within the orifice and encircled by the frame, wherein at least some of the fasteners of the set of fasteners are formed from a material displaying one or more shape-changing properties, wherein the one or more shape-changing properties comprises a transition from a deformed phase to a non-deformed phase, wherein the set of fasteners emerges from a side wall of the frame and extends radially inward from the side wall into the orifice to form an inscribed circle with tips of the set of fasteners.

2. The tissue capture device of claim 1, wherein at least some of the fasteners of the set of fasteners comprises a memory metal.

3. The tissue capture device of claim 2, wherein at least some of the fasteners of the set of fasteners comprise a memory metal micro-needle.

4. The tissue capture device of claim 2, wherein the deformed phase of the at least some of the fasteners of the set of fasteners is a martensite phase of the memory metal and the non-deformed phase of the at least some of the fasteners of the set of fasteners is an austenite phase of the memory metal.

5. The tissue capture device of claim 1, wherein the transition from the deformed phase to the non-deformed phase comprises:

a transition from the deformed phase to the non-deformed phase during tissue attachment, wherein the deformed phase occurs prior to tissue attachment.

6. The tissue capture device of claim 1, wherein each fastener of the set of fasteners comprises a length to width aspect ratio of 11:1.

7. The tissue capture device of claim 1, wherein the frame comprises an outer diameter to orifice diameter aspect ratio of 3:2.

8. The tissue capture device of claim 1, wherein the frame comprises a polymethyl methacrylate material.

9. The tissue capture device of claim 1, wherein the frame comprises a first frame portion and a second frame portion.

10. The tissue capture device of claim 9, wherein each fastener of the set of fasteners is positioned between the first frame portion and the second frame portion.

11. The tissue capture device of claim 9, wherein the first frame portion and the second frame portion are constructed via an additive manufacturing process.

12. The tissue capture device of claim 1, further comprising:

a medical device disposed over a surface of the frame.

13. The tissue capture device of claim 12, wherein the medical device comprises a biometric sensor.

14. The tissue capture device of claim 12, wherein the medical device comprises a drug delivery device.

15. A capsule endoscopy system, comprising:

a tissue capture device, the tissue capture device comprising:

a frame, wherein the frame defines an orifice; and a set of fasteners disposed within the orifice and encircled by the frame, wherein at least some of the fasteners of the set of fasteners are formed from a material displaying one or more shape-changing properties, wherein the one or more shape-changing properties comprises a transition from a deformed phase to a non-deformed phase, wherein the set of fasteners emerges from a side wall of the frame and extends radially inward from the side wall into the orifice to form an inscribed circle with tips of the set of fasteners; and a capsule endoscope, wherein the tissue capture device is coupled to the capsule endoscope.

16. The capsule endoscopy system of claim 15, wherein the capsule endoscope further comprises at least one of a data collection device configured to collect data from a gastrointestinal (GI) tract or a medical device configured to administer a treatment within the GI tract.

17. The capsule endoscopy system of claim 16, further comprising:

at least one exterior receiver communicatively coupled to the capsule endoscope, wherein the exterior receiver is configured to collect data from the capsule endoscope.

18. A method, comprising:

introducing a capsule endoscope to a gastrointestinal (GI) tract, wherein a tissue capture device is coupled to the capsule endoscope, wherein the tissue capture device comprises:

a frame, wherein the frame defines an orifice; and a set of fasteners disposed within the orifice and encircled by the frame, wherein at least some of the fasteners of the set of fasteners are formed from a material displaying one or more shape-changing properties wherein the one or more shape-changing properties comprises a transition from a deformed phase to a non-deformed phase, wherein the set of fasteners emerges from a side wall of the frame and extends radially inward from the side wall into the orifice to form an inscribed circle with tips of the set of fasteners;

reaching an area of interest within the GI tract;

inserting the set of fasteners of the tissue capture device into tissue of the GI tract in the area of interest, wherein the fasteners are inserted into the tissue in the deformed phase; and securing the tissue capture device to the tissue of the GI tract by transitioning the set of fasteners of the tissue capture device from the deformed phase to the non-deformed phase.

19. The method of claim 18, further comprising:

decoupling the tissue capture device from the capsule endoscope.

* * * * *